United States Patent
Khasnobish et al.

(10) Patent No.: US 11,550,049 B2
(45) Date of Patent: Jan. 10, 2023

(54) METHOD AND SYSTEM FOR UNOBTRUSIVE LIVELINESS DETECTION AND MONITORING USING DFR IN AN IOT NETWORK

(71) Applicant: Tata Consultancy Services Limited, Mumbai (IN)

(72) Inventors: Anwesha Khasnobish, Kolkata (IN); Arindam Ray, Kolkata (IN); Smriti Rani, Kolkata (IN); Amit Swain, Bangalore (IN); Chirabrata Bhaumik, Kolkata (IN); Tapas Chakravarty, Kolkata (IN)

(73) Assignee: Tata Consultancy Services Limited, Mumbai (IN)

( * ) Notice: Subject to any disclaimer, the term of this patent is extended or adjusted under 35 U.S.C. 154(b) by 233 days.

(21) Appl. No.: 17/105,242

(22) Filed: Nov. 25, 2020

(65) Prior Publication Data
US 2021/0199796 A1    Jul. 1, 2021

(30) Foreign Application Priority Data
Nov. 29, 2019 (IN) .............................. 201921049199

(51) Int. Cl.
*G01S 13/88*    (2006.01)
*G01S 7/41*    (2006.01)
*G01S 13/02*    (2006.01)

(52) U.S. Cl.
CPC ............ *G01S 13/886* (2013.01); *G01S 7/415* (2013.01); *G01S 13/0209* (2013.01)

(58) Field of Classification Search
CPC .... G01S 13/886; G01S 7/415; G01S 13/0209; G01S 13/88; G01S 13/56; A61B 5/0002
See application file for complete search history.

(56) References Cited

U.S. PATENT DOCUMENTS

| 4,513,748 A | 4/1985 | Nowogrodzki et al. |
| 2008/0119716 A1* | 5/2008 | Boric-Lubecke .... A61B 5/7225 600/407 |

(Continued)

OTHER PUBLICATIONS

H. Shen et al., "Respiration and Heartbeat Rates Measurement Based on Autocorrelation Using IR-UWB Radar," in IEEE Transactions on Circuits and Systems II: Express Briefs, vol. 65, No. 10, pp. 1470-1474, Oct. 2018, doi: 10.1109/TCSII.2018.2860015. (Year: 2018).*

(Continued)

*Primary Examiner* — Erin F Heard
*Assistant Examiner* — Juliana Cross
(74) *Attorney, Agent, or Firm* — Finnegan, Henderson, Farabow, Garrett & Dunner, LLP

(57) ABSTRACT

Radar based HR and BR measurements by simultaneous decoding is a technical problem due to presence of intermodulation of BR and HR harmonics, which degrades simultaneous decoding. Embodiments herein provide a method and system for unobtrusive liveliness detection and monitoring of a subject using a Dual Frequency Radar (DFR) in an IOT network. The system has the capability to completely process the captured raw signals onboard to by applying required signal conditioning and extraction of relevant information using unique signal processing techniques for determining the HR and the BR of the subject accurately. The intermodulation of BR and HR harmonics is eliminated by the system by performing frequency spectrum averaging of both radars signals, which improves the accuracy. Further, the system is configured with a light MQTT protocol and encoding modules for any data to be shared for off board processing, ensuring data security and privacy compliance.

15 Claims, 12 Drawing Sheets

(56) References Cited

U.S. PATENT DOCUMENTS

| | | | | |
|---|---|---|---|---|
| 2009/0227882 | A1* | 9/2009 | Foo | A61B 5/7207 |
| | | | | 343/893 |
| 2010/0286533 | A1* | 11/2010 | Lee | A61B 5/02444 |
| | | | | 600/484 |
| 2018/0053393 | A1* | 2/2018 | White | A61B 5/7278 |
| 2019/0015277 | A1* | 1/2019 | Sauser | A61G 7/05769 |
| 2019/0183352 | A1* | 6/2019 | Regev | G01S 13/536 |
| 2021/0275056 | A1* | 9/2021 | McMahon | A61B 5/6887 |

OTHER PUBLICATIONS

Shen, Hongming et al., "Respiration and Heartbeat Rates Measurement Based on Autocorrelation Using IR-UWB Radar", Transactions on Circuits and Systems II, 2018, IEEE, http://users.wpi.edu/~xhuang/pubs/2018_shen_tcas2.pdf.

Suzuki, Satoshi et al., "A non-contact vital sign monitoring system for ambulances using dual-frequency microwave radars", Medical & Biological Engineering & Computing, 2008, Springer, https://pdfs.semanticscholar.org/739a/54384e3b42bc6525e511385cbbf350f63341.pdf.

Jelen, M et al., "Multi-frequency sensor for remote measurement of breath and heartbeat", Advances in Radio Science, 2006, Researchgate, http://67.225.133.110/~gbpprorg/mil/cavity/ars-4-79-2006.pdf.

Chioukh, Lydia et al., "Multi-frequency Radar Systems for Monitoring Vital Signs", Asia-Pacific Microwave Conference, 2010, IEEE, https://www.researchgate.net/publication/250927093_Multi-frequency_radar_systems_for_monitoring_vital_signs/link/00b7d51f86b74d151d000000/download.

* cited by examiner

METHOD AND SYSTEM FOR UNOBTRUSIVE LIVELINESS DETECTION AND MONITORING USING DFR IN AN IOT NETWORK

PRIORITY CLAIM

This U.S. patent application claims priority under 35 U.S.C. § 119 to: the Indian patent application no. 201921049199, filed on Nov. 29, 2019. The entire contents of the aforementioned application are incorporated herein by reference.

TECHNICAL FIELD

The embodiments herein generally relate to the field of unobtrusive vital signs detection and monitoring and, more particularly, to method and system for unobtrusive liveliness detection and monitoring of a subject using a Dual Frequency Radar (DFR) in an Internet of Things (IOT) network.

BACKGROUND

Vital signs are most important medical signs that indicate status of a body's vital functions body temperature, blood pressure, pulse (heart rate), and breathing rate (respiratory rate), and often notated as BT, BP, HR, and BR. Seamless detection and monitoring of these vital signs, typically the HR and BR is necessary to seamlessly track health condition of subjects who are diseased, very old aged, stay lonely. Radar based vital signs monitoring, which provides an unobtrusive sensing, is gaining importance with rapid development in sensing technology with small size, low cost radar set ups. Further, radar-based sensing, unlike camera based sensing, does not affect the privacy of the subject and enables vital sign detection and monitoring remotely.

Conventionally single frequency radars have been used for non-contact sensing of vital signs. However, a single frequency radar fails to accurately capture signal due to two distinct movements such as chest movement due to breathing and due to heartbeat. Attempts have been made to improve the accuracy of radar based sensing of vital signs using different types of radars and with different set ups such a twin frequency radars, triple frequency radar set ups using Continuous Wave (CW) radars, Impulse radio ultra-wideband (IR-UWB) radars and the like in a sensor module assembly. One of the technical problems lies in capturing signals associated with the HR and BR measurement simultaneously, detecting them distinctly and estimating the HR and BR accurately. Accuracy in HR and BR measurements is a challenge since these signals are derived from chest movement or activity of the subject, which is a lower frequency range (0 to 2 Hz) phenomenon with low amplitudes and are associated high noise presence. Further, the challenge is to transmit the captured data or signals associated while maintaining data privacy and security. Each of the existing radar-based sensing works in the literature has used different approaches to address preprocessing of the signal captured by the radar for noise reduction and clutter removal. Further different approaches have been used to further process the radar signals to extract the vital signs or measurements of HR, BR and the like. However, each existing approach has limitations affecting the accuracy, cost of HR and BR detection and monitoring. For example, existing UWB systems are hard to implement in real time scenarios. They also need complex hardware for signal generation and receipt, and may also be prone to environmental clutter. Another, existing three radar system approach requires reorientation of individual radars with respect to reach other. Further, requires complex triangulation methods in order to decipher the required information.

Further, accuracy of the vital signs or biosignals measurements such as the HR and the BR and the like, extracted from the radar signals, is critical factor for remote health monitoring to be completely reliable on such sensing. Thus, approaches used to handle preprocessing and processing of the radar signals to extract more and more accurate HR and BR to the requirements of clinical measurement standards are desirable to completely rely on such remote monitoring. However, there exists a challenge during simultaneous measurement of HR and BR due to presence of intermodulation of BR and HR harmonics, which degrades simultaneous decoding of both. Further, in an Internet of Things (IOT) network environments providing radar sensing based remote monitoring of vital signs, processing of raw biosignals sensed via a sensor module or node, conventionally takes place in a cloud network. The reason being, sensor module has limitation in processing capability and battery power. However, processing of raw signals into the cloud adds to latency in computation and may not be desirable, where quick actions or alerts need to be initiated for any major fluctuations in a subject's vital signs. Attempts have been made to perform processing of raw radar signals to extract the measurement at sensing end. Moreover, it is equally important to gather the data collected by sensors, whether raw or processed, over a prolonged period for further data analytics. Thus, it is necessary that sensors have the capability to share clinical data of the subject periodically to the cloud network, while ensuring compliancy with data security and privacy policies. Thus, data encryption, communication protocols used, and interfaces used for securely transmitting data need to be lightweight considering limitations in sensor (edge) capabilities in the IOT network.

SUMMARY

Embodiments of the present disclosure present technological improvements as solutions to one or more of the above-mentioned technical problems recognized by the inventors in conventional systems. For example, in one embodiment, a processor implemented method for unobtrusive liveliness detection and monitoring using a Dual Frequency Radar (DFR) in an Internet of Things (IOT) network is provided. The method comprising receiving a first channel signal captured by a first radar of the DFR and a second channel signal captured by a second radar of the DFR, wherein the first radar operates at a first frequency designed to capture chest movement of a subject due to heartbeat activity and the second radar operates at a second frequency designed to capture chest movement of the subject due to breathing activity, and wherein the DFR is positioned to cover an observation space for liveliness monitoring of the subject present in the observation space; segmenting in time domain each of the first channel signal and the second channel signal into a plurality of segments in accordance with a predefined segment interval, wherein the predefined segment interval is selected to cover time corresponding to at least two breathing cycles; transmitting the plurality of segments of the first channel signal and the second channel signal to a hardware preprocessing block to perform a first preprocessing on the plurality of segments of the first channel signal and the second channel signal to provide signal conditioning; receiving from the hardware preprocessing block the first preprocessed plurality of segments of the first channel signal and the second channel signal; sequentially performing a second preprocessing on the first preprocessed plurality of segments of the first channel signal and the second channel signal for signal conditioning and residual noise elimination using a software processing block; analyzing each of the second preprocessed plurality of segments associated with the first channel signal and the second channel signal to detect a plurality of presence segments indicative of a presence of subject or one or more absence segments indicative of absence of the subject in the observation space based on a presence detection technique, wherein the detected one or more absence segments are discarded; detecting a quality of each of the plurality of presence segments by computing an Area Under Correlation (AUC) of each of the plurality of presence segments, wherein one or more segments among the plurality presence segments having the AUC below a first AUC threshold are discarded; determining whether the AUC of each of the plurality of presence segments, having the AUC above or equal to the first AUC threshold, are i) above or ii) equal or below a second AUC threshold, wherein a first set of presence segments among the plurality of presence segments having the AUC above the second AUC threshold are utilized for simultaneously determining a Hear Rate (HR) and a Breath Rate (BR) of the subject to detect and monitor the liveliness of the subject; and a second set of presence segments among the plurality of presence segments having the AUC below or equal to the second AUC threshold is utilized for determining the BR rate to detect and monitor the liveliness of the subject; and generating an alert for at least one of: i) if the determined HR is below a Liveliness HR threshold, and ii) if the determined BR is below a liveliness BR threshold.

In another aspect, a system for unobtrusive liveliness detection and monitoring using a Dual Frequency Radar (DFR) in an Internet of Things (IOT) network is provided. The system comprises a memory storing instructions; one or more Input/Output (I/O) interfaces; and one or more hardware processors coupled to the memory via the one or more I/O interfaces, wherein the one or more hardware processors are configured by the instructions to receive a first channel signal captured by a first radar of the DFR and a second channel signal captured by a second radar of the DFR, wherein the first radar operates at a first frequency designed to capture chest movement of a subject due to heartbeat activity and the second radar operates at a second frequency designed to capture chest movement of the subject due to breathing activity, and wherein the DFR is positioned to cover an observation space for liveliness monitoring of the subject present in the observation space; segment in time domain each of the first channel signal and the second channel signal into a plurality of segments in accordance with a predefined segment interval, wherein the predefined segment interval is selected to cover time corresponding to at least two breathing cycles; transmit the plurality of segments of the first channel signal and the second channel signal to a hardware preprocessing block to perform a first preprocessing on the plurality of segments of the first channel signal and the second channel signal to provide signal conditioning; receive from the hardware preprocessing block the first preprocessed plurality of segments of the first channel signal and the second channel signal; sequentially performing a second preprocessing on the first preprocessed plurality of segments of the first channel signal and the second channel signal for signal conditioning and residual noise elimination using a software processing block; analyze each of the second preprocessed plurality of segments associated with the first channel signal and the second channel signal to detect a plurality of presence segments indicative of a presence of subject or one or more absence segments indicative of absence of the subject in the observation space based on a presence detection technique, wherein the detected one or more absence segments are discarded; detect a quality of each of the plurality of presence segments by computing an Area Under Correlation (AUC) of each of the plurality of presence segments, wherein one or more segments among the plurality presence segments having the AUC below a first AUC threshold are discarded; determine whether the AUC of each of the plurality of presence segments, having the AUC above or equal to the first AUC threshold, are i) above or ii) equal or below a second AUC threshold, wherein a first set of presence segments among the plurality of presence segments having the AUC above the second AUC threshold is utilized for simultaneously determining a Hear Rate (HR) and a Breath Rate (BR) of the subject to detect and monitor the liveliness of the subject; and a second set of presence segments among the plurality of presence segments having the AUC below or equal to the second AUC threshold are utilized for determining only the BR rate to detect and monitor the liveliness of the subject; and generate an alert for at least one of: i) if the determined HR is below a Liveliness HR threshold, and ii) if the determined BR is below a liveliness BR threshold.

In yet another aspect, there are provided one or more non-transitory machine readable information storage mediums comprising one or more instructions, which when executed by one or more hardware processors causes a method for unobtrusive liveliness detection and monitoring using a Dual Frequency Radar (DFR) in an Internet of Things (IOT) network is provided. The method comprising receiving a first channel signal captured by a first radar of the DFR and a second channel signal captured by a second radar of the DFR, wherein the first radar operates at a first frequency designed to capture chest movement of a subject due to heartbeat activity and the second radar operates at a second frequency designed to capture chest movement of the subject due to breathing activity, and wherein the DFR is positioned to cover an observation space for liveliness monitoring of the subject present in the observation space; segmenting in time domain each of the first channel signal and the second channel signal into a plurality of segments in accordance with a predefined segment interval, wherein the predefined segment interval is selected to cover time corresponding to at least two breathing cycles; transmitting the plurality of segments of the first channel signal and the second channel signal to a hardware preprocessing block to perform a first preprocessing on the plurality of segments of the first channel signal and the second channel signal to provide signal conditioning; receiving from the hardware preprocessing block the first preprocessed plurality of segments of the first channel signal and the second channel signal; sequentially performing a second preprocessing on the first preprocessed plurality of segments of the first channel signal and the second channel signal for signal conditioning and residual noise elimination using a software processing block; analyzing each of the second preprocessed plurality of segments associated with the first channel signal and the second channel signal to detect a plurality of presence segments indicative of a presence of subject or one or more absence segments indicative of absence of the subject in the observation space based on a presence detection technique, wherein the detected one or more absence segments are discarded; detecting a quality of each of the plurality of presence segments by computing an Area Under Correlation (AUC) of each of the plurality of presence segments, wherein one or more segments among the plurality presence segments having the AUC below a first AUC threshold are discarded; determining whether the AUC of each of the plurality of presence segments, having the AUC above or equal to the first AUC threshold, are i) above or ii) equal or below a second AUC threshold, wherein a first set of presence segments among the plurality of presence segments having the AUC above the second AUC threshold are utilized for simultaneously determining a Hear Rate (HR) and a Breath Rate (BR) of the subject to detect and monitor the liveliness of the subject; and a second set of presence segments among the plurality of presence segments having the AUC below or equal to the second AUC threshold is utilized for determining the BR rate to detect and monitor the liveliness of the subject; and generating an alert for at least one of: i) if the determined HR is below a Liveliness HR threshold, and ii) if the determined BR is below a liveliness BR threshold.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION OF EMBODIMENTS

Figure 1:
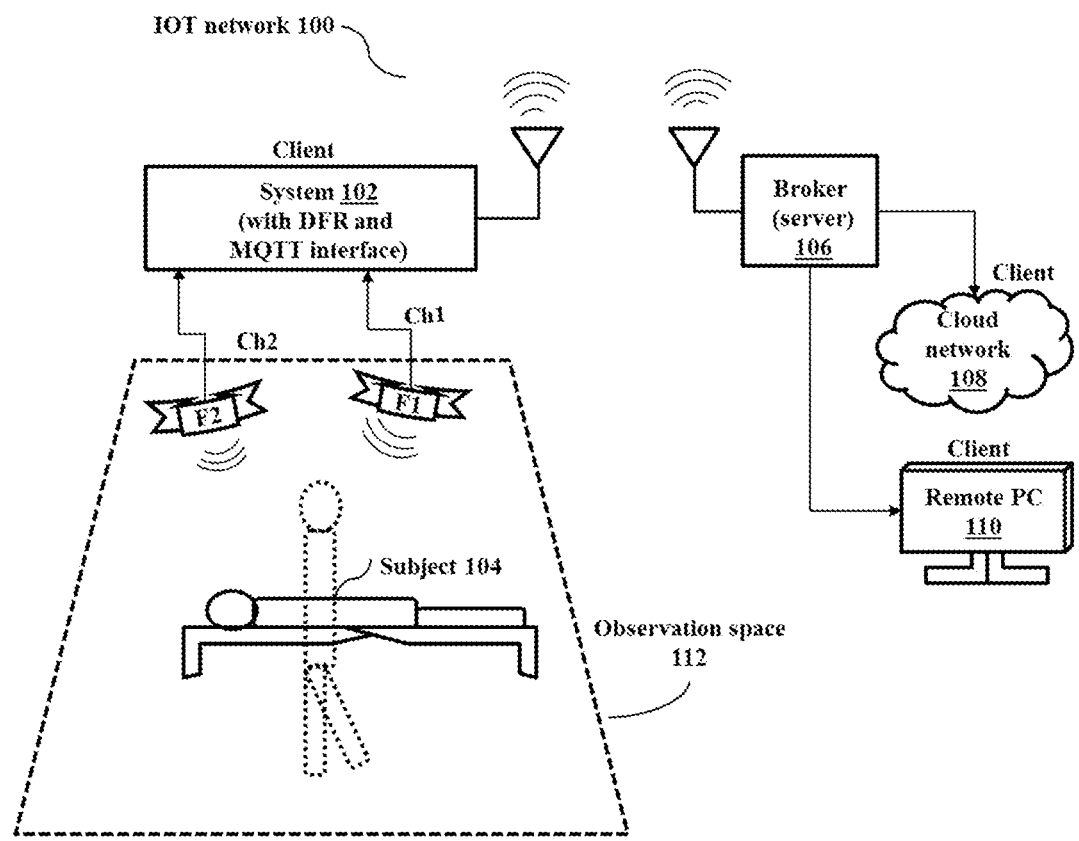
FIG. 1 is an example overview of an Internet of Things (IOT) network environment that implements a system for unobtrusive liveliness detection and monitoring of a subject using a Dual Frequency Radar (DFR), in accordance with some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

Radar based unobtrusive sensing for vital signs or bio-signal monitoring to estimate parameters such as a Heart Rate (HR), Breathe Rate (BR) is gaining importance. Embodiments herein provide a method and system for unobtrusive liveliness detection and monitoring of a subject using a Dual Frequency Radar (DFR) in an Internet of Things (IOT) network. The DFR is a set of two off the shelf different frequency radars. Liveliness referred herein indicates life signs shown by the subject, typically detecting activity such as limb or body movements, as well as presence of heart activity and breathing activity by monitoring chest movement of the subject. The system is equipped with the DFR to capture raw signals associated with the chest movement of the subject under observation. Further, the system has the capability to completely process the captured raw signals onboard to by applying required signal conditioning and extraction of relevant information using unique signal processing techniques for determining the HR and the BR of the subject accurately. The presence of intermodulation of BR and HR harmonics, which degrades simultaneous decoding of both, is eliminated by the system disclosed herein. To eliminate harmonics the system performs frequency spectrum averaging of both radars signals, which improves the accuracy.

Further, the system is configured with a light-weight communication protocol such as Message Queuing Telemetry Transport (MQTT). The system provides encryption modules for encrypting any data to be shared for off board to a distant data analytics system at predefined intervals for data analysis, processing and so on using the embedded MQTT interface provision, ensuring data security and privacy compliance. The system can be configured to choose onboard or off board processing, thus provide an option of remote data processing. So, in addition to the system being a liveliness monitored, it can also serve as a portable node for remote monitoring and maintaining continuous health records for subjects. The system can be implemented on a sensor node among a plurality of sensor nodes in the IOT network, thus providing a standalone sensor node with full processing capability along with securely data off boarding capability.

Referring now to the drawings, and more particularly to FIGS. 1 through 8, where similar reference characters denote corresponding features consistently throughout the figures, there are shown preferred embodiments and these embodiments are described in the context of the following exemplary system and/or method.

FIG. 1 is an example overview of an Internet of Things (IOT) network environment 100 that implements a system 102 for unobtrusive liveliness detection and monitoring of a subject 104 using a Dual Frequency Radar (DFR), in accordance with some embodiments of the present disclosure. As depicted, the system 102, interchangeably referred as a sensor node 102, is a sensor node among a plurality of nodes of the IOT network 100. The system 102 is configured to monitor the HR and the BR of the subject 104, indicative of liveliness of the subject, present within an observation space 112. As understood, the observation space is defined by coverage range of two individual radars of the DFR. Each of the radar captures signal, also referred as raw data, over two individual radar channel signals such a Channel I (Ch1) and Channel 2 (Ch2). The processing of the channel signals comprises a hardware processing, followed by a software processing and then final processing to determine the HR and the BR of the subject 104. The system 102 can be configured with two options, wherein in one option the completely processed data can be encrypted and communicated to a cloud network 108 or a remote data analytics system such as a cloud network 108 or a remote PC 110 for further data analytics. In another option, the system 102 can be configured to pre-process the raw data using a first hardware preprocessing step, then encrypt the pre-processed data and off board minimally processed data to the data analytic system to perform remote data entire processing. The system 102 is configured with the MQTT interface operating in client server client model, wherein a broker or a server 106 facilitates the data transfer between a client (system 102) and the remote end client (the data analytic system such as a cloud server 108 or a remote PC 110) using the MQTT communication protocol. The functions of the system 102 are explained in conjunction with functional modules of the system 102 depicted in FIG. 2 and data processing by the system 102 as explained in conjunction with FIGS. 3 through 8.

Figure 2:
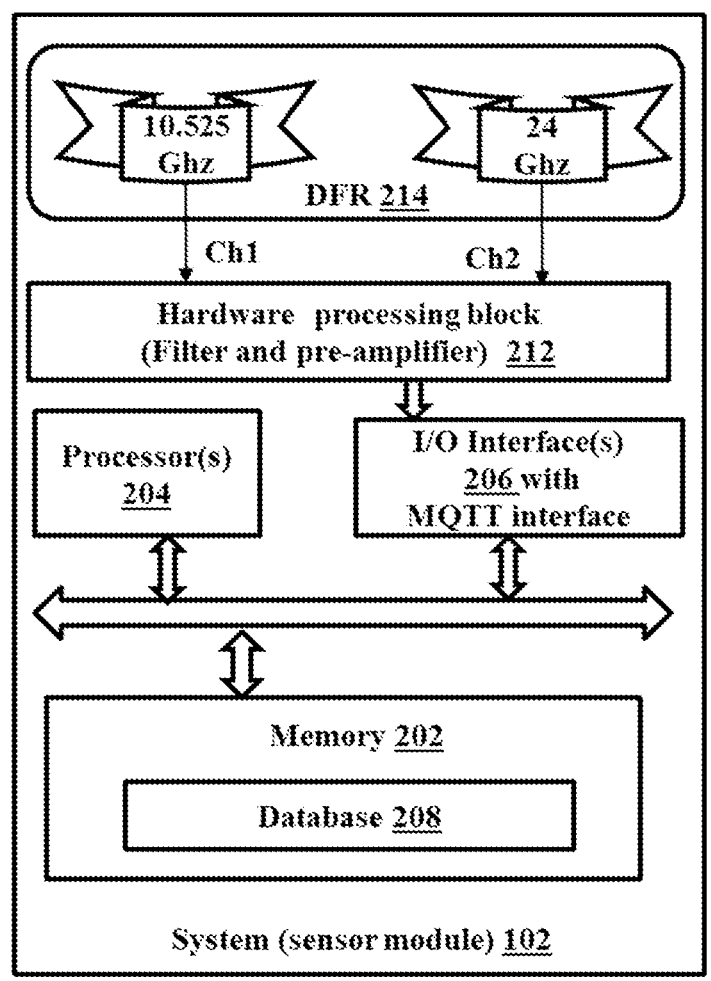
FIG. 2 is a functional block diagram of the system, depicted in FIG. 1, for unobtrusive liveliness detection and monitoring of the subject using the DFR in the IOT environment, in accordance with some embodiments of the present disclosure.

FIG. 2 is a functional block diagram of the system 102 of in FIG. 1, and interchangeably referred sensor node 102, for unobtrusive liveliness detection and monitoring of the subject using the DFR in the IOT network 100, in accordance with some embodiments of the present disclosure.

In an embodiment, the system 102 includes a processor(s) 204, communication interface(s), alternatively referred as input/output (I/O) interface(s) 206, and one or more data storage devices or a memory 202 operatively coupled to the processor(s) 204. In an embodiment, the processor(s) 204, can be one or more hardware processors 204. In an embodiment, the one or more hardware processors 204 can be implemented as one or more microprocessors, microcomputers, microcontrollers, digital signal processors, central processing units, state machines, logic circuitries, and/or any devices that manipulate signals based on operational instructions. In an example implementation, the processor (s) 204 can be a Raspberry-pi™ processor. Among other capabilities, the one or more hardware processors 204 are configured to fetch and execute computer-readable instructions stored in the memory 202. In an embodiment, the system 102 can be implemented in a variety of computing systems, which have integrated DFR sensing such as the DFR 214 or can provide external plugin of DFRs.

Figure 7A:
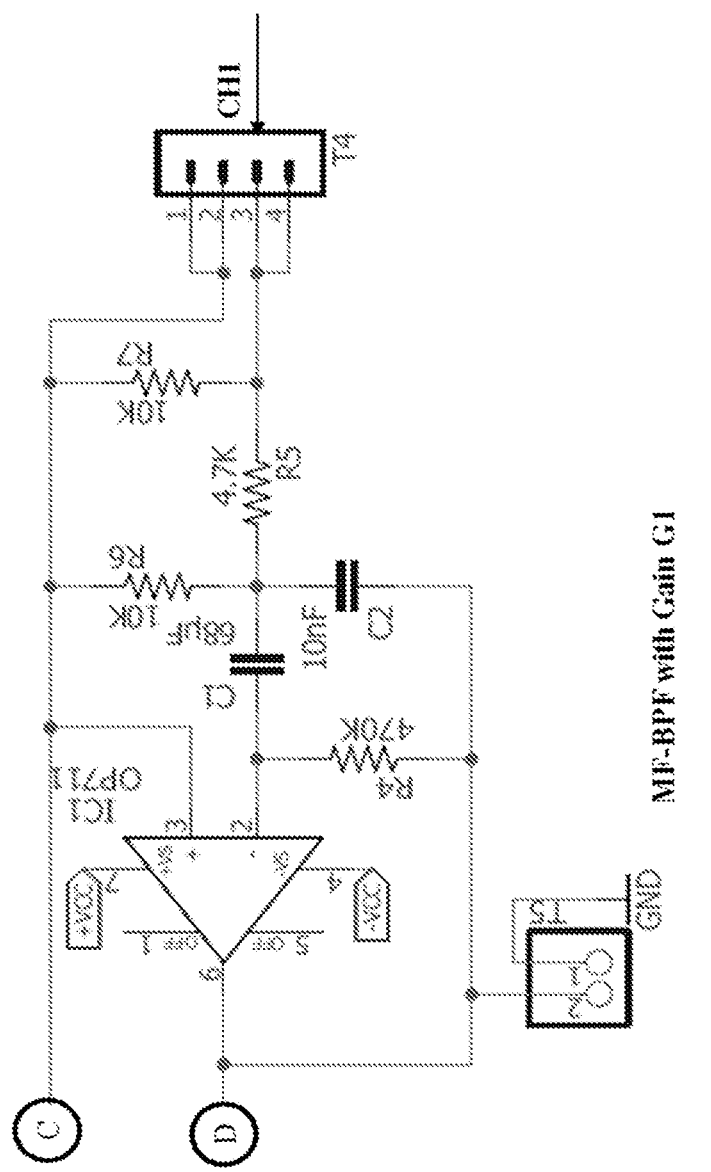
FIG. 7A through 7C is an exemplary design of the hardware processing block depicted in FIG. 6 depicting hardware circuit for a single channel, in accordance with some embodiments of the present disclosure.
Figure 7B:
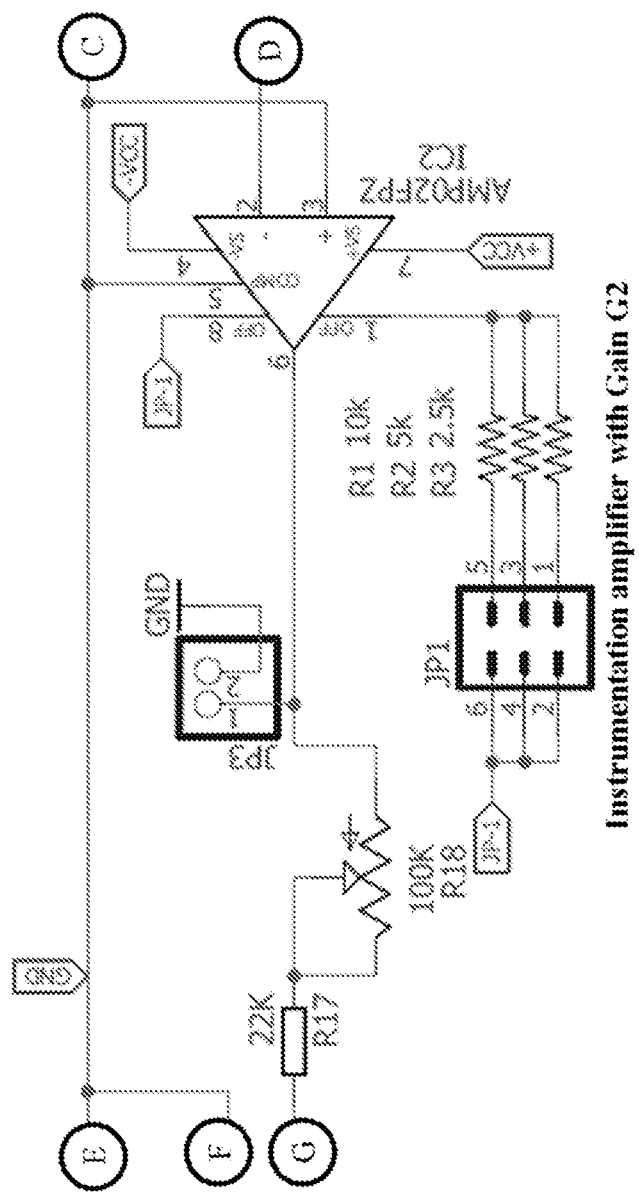
Figure 7C:
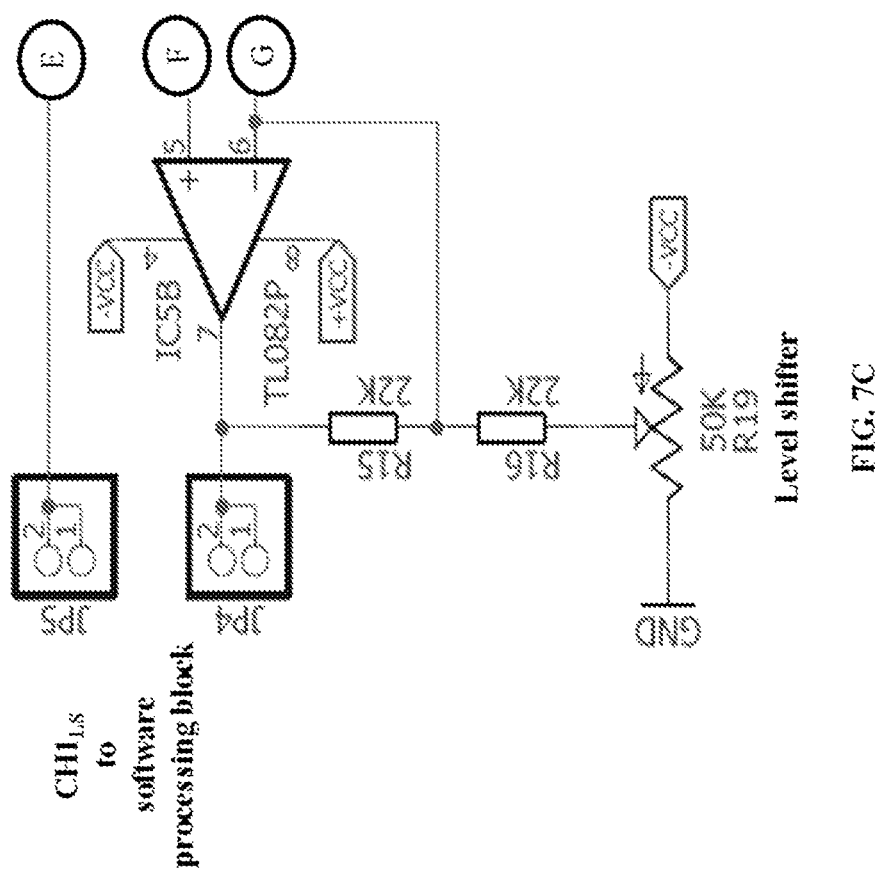

The I/O interface(s) 206 can include a variety of software and hardware interfaces, for example, a web interface, a graphical user interface, the MQTT interface and the like and can facilitate multiple communications within a wide variety of networks N/W and protocol types, including wired networks, for example, LAN, cable, etc., and wireless networks, such as WLAN, cellular, or satellite. In an embodiment, the I/O interface (s) 206 can include one or more ports for connecting a number of devices to one another or to another server. The I/O interface 206, in this case MQTT interface enables communication, via the broker 106, with the cloud network 108 or the remote PC 110 for off-board processing. Further, the I/O interface(s) 206 enables receiving the channel signals (Ch1 and Ch2) from two radars depicted in the DFR 214 block post hardware preprocessing provided by a hardware processing block 212. The hardware pre-processing block 212 provides preliminary signal conditioning. The function blocks of the hardware processing block 212 are explained in conjunction with FIG. 7A through 7C depicting cascaded combination of a hardware multi-feedback filter (MF-BPF) or simply referred as MF-BPF, an instrumentation amplifier and a level shifter. In an embodiments, the DFR 214 can be a set of two Continuous Wave (CW) radars placed side by side and positioned to capture radar signals reflected from the subject 104, with Ch1 radar operating at a first frequency of 10.525 GigaHz (GHz) and Ch2 radar operating at a second frequency of 24 GHz. Thus, the system 102 disclosed provides the DFR 214 as an enclosure, where the two radars are placed side by side, with their center aligned. This complete enclose (DFR 214) can transmit and receive the signals from a target, for example (e.g., subject 104). Thus, unlike many existing multi-radar assemblies, the system 102 does not require a reorientation of individual radars with respect to reach other. For example, in existing three radar systems there is need of complex triangulation methods in order to decipher the required information, however with usage of the DFR 214, the system 102 disclosed herein is implemented using simple, lightweight yet effective algorithm for signal processing, which is real time and is suitable for embedded platforms. This the system disclosed is edge/cloud compatible. Further, unlike existing Ultra-wide band (UWB) radar based sensing approaches, which are hard to implement in real time scenarios, need complex hardware for signal generation and receipt, and are also prone to environmental clutter, the system 102 disclosed herein has a complete modular architecture and thus has the flexibility in adding more sensor or edge/cloud components.

The first radar majorly captures chest movement of the subject 104 due to heartbeat activity and the second radar majorly captures chest movement of the subject due to breathing activity. However, some frequency components associated with the HR and BR may be present in either channels, hence both channels signals are considered by the system 102 while computing HR and BR. To elaborate further, the 24 GHz radar is most suitable for HR but it contains BR information or frequency components as well. The 10.525 GHz radar has more Signal to Noise ratio (SNR) for the BR, however for HR the SNR is less, but still the 10.525 radar captures HR information. For the above reasons, the system 102 utilizes signals from the two radars presence detection and BR/calculation, effectively providing accurate BR or HR measurements.

Further, the memory 202 may include various modules such as the software processing block (not shown) to perform signal conditioning and residual noise elimination of the channel signals. The software processing module further processes channel signals for presence detection of the subject in the observation space 112 and computation of the HR and the BR by extracting information from the preprocessed channel signals using signal processing techniques. The sub modules of software processing block and their functionalities is further explained in conjunction with FIG.

8. The memory may also include a database 208, that may store or record the processed channel signals and the determined HR and BR computed seamlessly by the system 102. The memory 202 may further include encryption or encoding modules (not shown) that encode the data to be shared off-board to a remotely located data analytics system. In an embodiment, the database 208 may be external (not shown) to the system 102. The memory 202 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. Thus, the memory 202 may comprise information pertaining to input(s)/output(s) of each step performed by the processor(s) 204 of the system 102 and methods of the present disclosure. Functions of the components of system 102 are explained in conjunction with method steps of flow diagram depicted in FIG. 3A through 3C and FIG. 4 through FIG. 8.

Figure 3A:
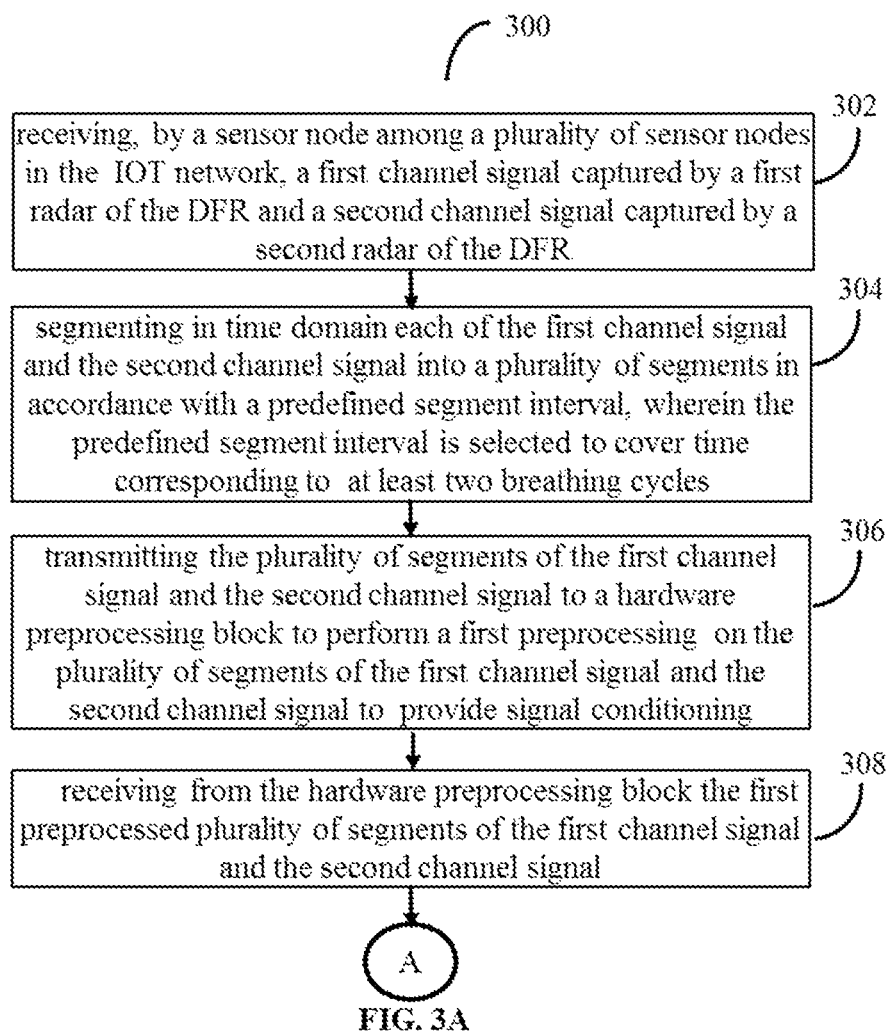
FIGS. 3A, 3B and 3C depict a flow diagram illustrating a method, implemented using the system of FIG. 2 in the IOT network environment, for unobtrusive liveliness detection and monitoring of the subject using the DFR, in accordance with some embodiments of the present disclosure.
Figure 3B:
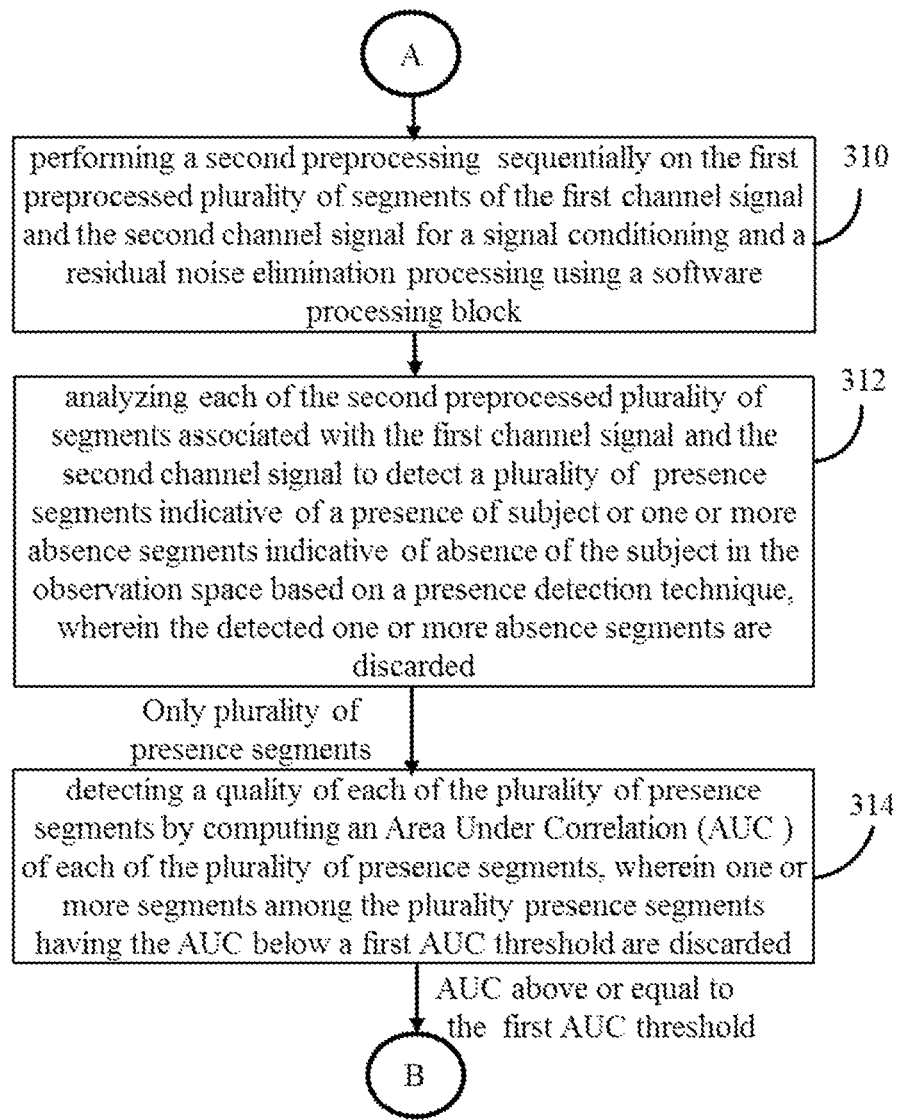
Figure 3C:
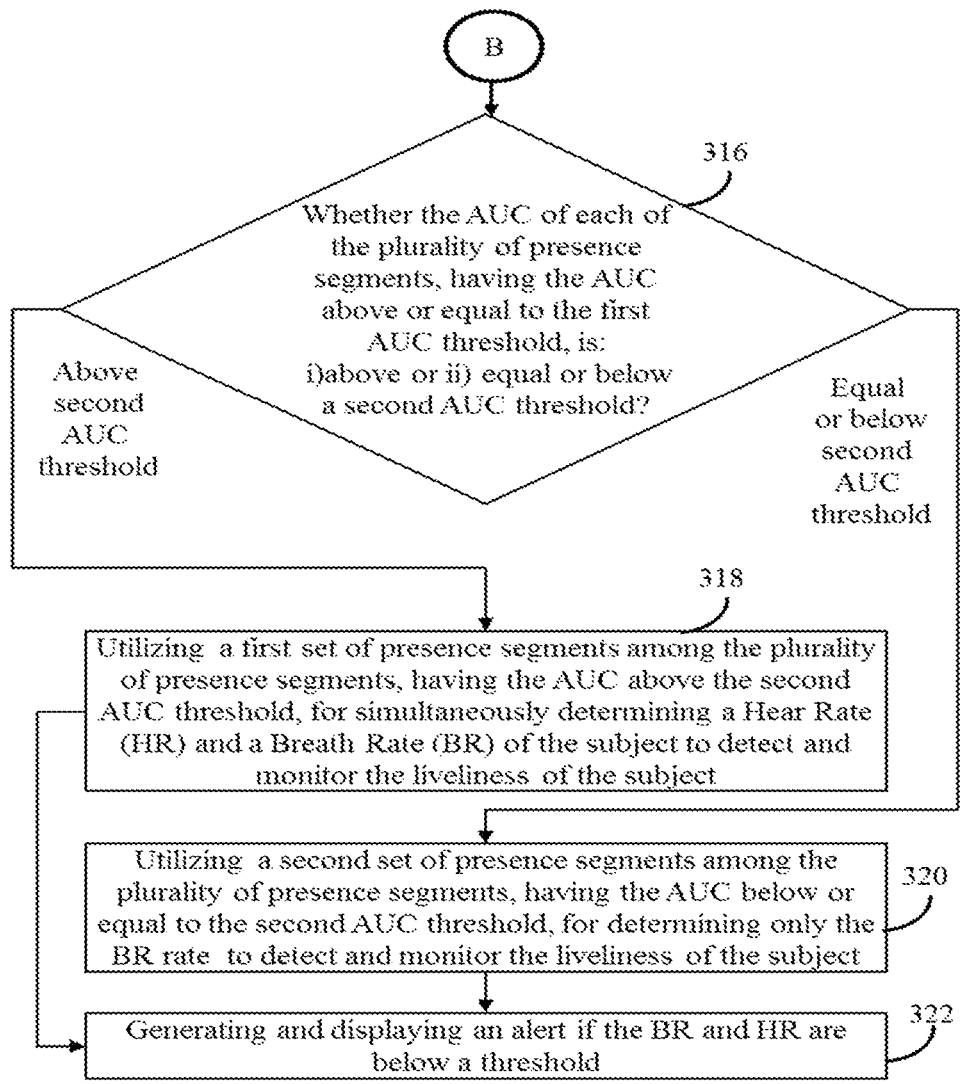
Figure 4:
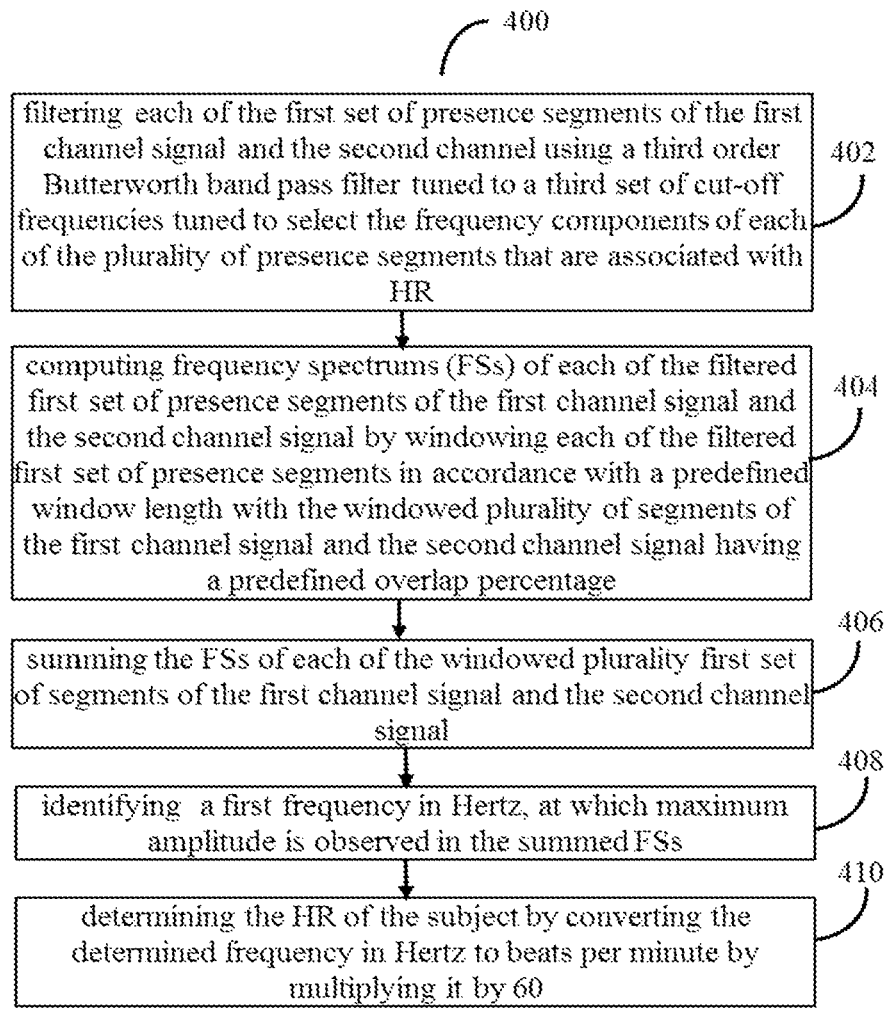
FIG. 4 illustrates a flow diagram of a process, for determining a Heart Rate (HR) of the subject under observation, utilized by the method of the flow diagram of FIGS. 3A, 3B and 3C implemented via the system of FIG. 2, in accordance with some embodiments of the present disclosure.
Figure 5:
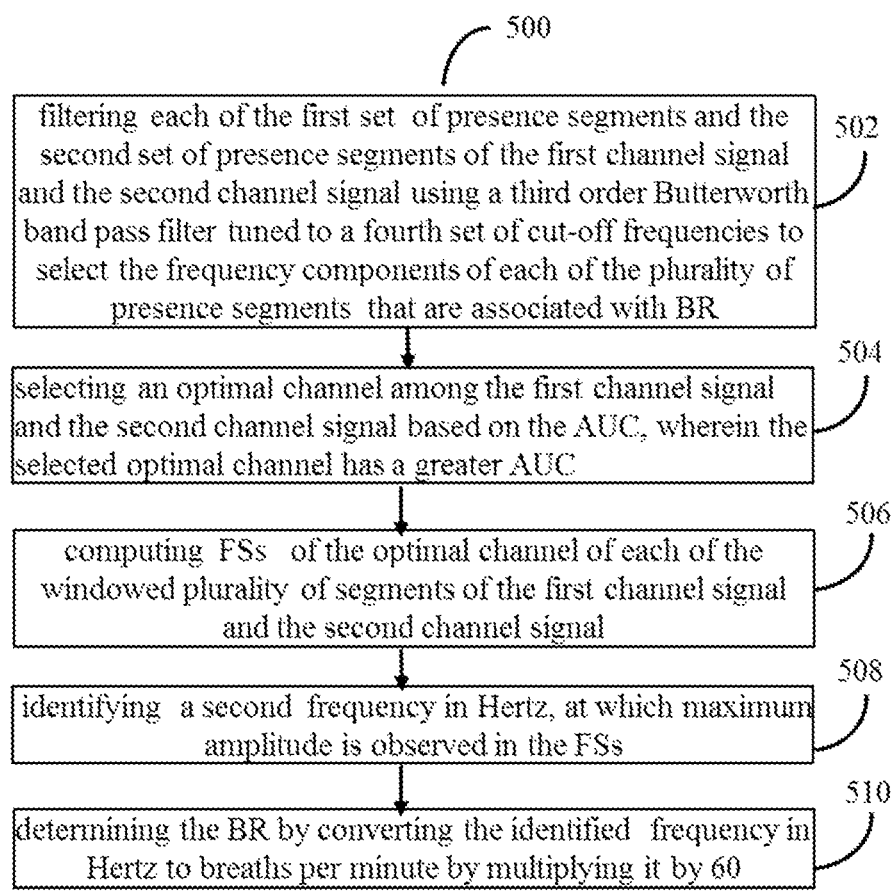
FIG. 5 illustrates a flow diagram of a process, for determining a Breathing Rate (BR) of the subject under observation, utilized by the method depicted by the flow diagram of FIGS. 3A, 3B and 3C implemented via the system of FIG. 2, in accordance with some embodiments of the present disclosure.
Figure 6:
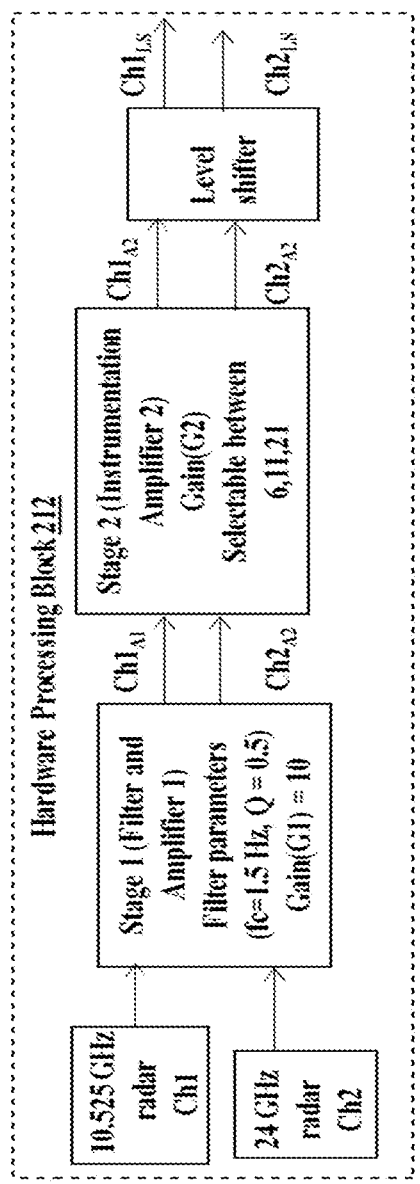
FIG. 6 depicts a hardware processing block of the system of FIG. 2 for preprocessing of signals captured by the two radars of the DFR, in accordance with some embodiments of the present disclosure.

FIGS. 3A, 3B and 3C depict a flow diagram illustrating a method 300, implemented using the system of FIG. 2, for unobtrusive liveliness detection and monitoring of the subject using the DFR 214 in the IOT network 100, in accordance with some embodiments of the present disclosure. In an embodiment, the system 102 comprises one or more data storage devices or the memory 202 operatively coupled to the processor(s) 204 and is configured to store instructions for execution of steps of the method 300 by the processor(s) 204. The steps of the method 300 of the present disclosure will now be explained with reference to the components or blocks of the system 102 as depicted in FIG. 2 and the steps of flow diagram as depicted in FIG. 3 through FIG. 5 with reference to FIGS. 6 through 8. Although process steps, method steps, techniques or the like may be described in a sequential order, such processes, methods and techniques may be configured to work in alternate orders. In other words, any sequence or order of steps that may be described does not necessarily indicate a requirement that the steps to be performed in that order. The steps of processes described herein may be performed in any order practical. Further, some steps may be performed simultaneously.

Referring to the steps of the method 300, at step 302, the one or more hardware processors 204 of the system 102 (the sensor node 102) are configured to receive a first channel signal (Ch1) captured by a first radar of the DFR and a second channel signal (CH2) captured by a second radar of the DFR, wherein the first radar operates at a first frequency (10.525 GHz) that can captures a major frequency components associated with the chest movement of a subject due to heartbeat activity and the second radar operates at a second frequency (24 GHz that captures major frequency component associated with the chest movement of the subject due to breathing activity. The DFR is positioned to cover an observation space such as the observation space 112 for liveliness monitoring of the subject present in the observation space, wherein the two radars can be placed side by side. At step 304 the one or more hardware processors 204 are configured to segment in time domain each of the first channel signal and the second channel signal into a plurality of segments in accordance with a predefined segment interval. The predefined segment interval is selected to cover time corresponding to at least two breathing cycles. The incoming signal streams from the two channels are broken down (or segmented) into smaller sequences, each of which has a duration of 10 seconds, by making use of a windowing function. This is a suitable choice as a complete breathing cycle can last up to 5 s, and as such a minimum of two cycles are required to correctly detect the underlying frequencies resent in the sequence.

Once segmented, at step 306 of the method 300 the one or more hardware processors (204) are configured to forward (or transmit) the plurality of segments of the first channel signal and the second channel signal to a hardware preprocessing block to perform a first preprocessing on the plurality of segments of the first channel signal and the second channel signal to provide first level signal conditioning. The first preprocessing comprises steps a) and b) as follows:

a) filtering the plurality of segments of each of the first channel signal and the second channel using the hardware multi-feedback band pass filter (MF-BPF), wherein a first set of cut-off frequencies of the hardware band pass filter are tuned to capture frequency components corresponding to the chest movement due to the breathing activity and the heartbeat activity of the subject and eliminate inherent DC component present in the first channel signal and the second channel signal of the DFR. The multi-feedback band pass filter or MF-BPF has a center frequency (fc)=1.5 Hz and Q (Quality factor)=0.5 as depicted in the hardware processing block of FIG. 6, thus providing a theoretical bandwidth (BW) is 0 to 3 Hz. Since both the BR and HR signals are very low frequency signals (<2 Hz), thus in order to extract the required information, the prerequisite is to eliminate the DC completely and have a sharp roll off filtering, with high quality factor (Q). These are not achievable in hardware domain with simple band pass filters. Thus MF-BPF, designed for the system 102, provides sufficiently high Q, and is also capable of filtering the signal of concerned BW (i.e., 0.2-2 Hz). However, the MF-BPF is a lower order hardware filter, hence practical limitation is that the cut off frequencies are not be ideal, rather the frequency response will have slow roll offs. Thus, for the same reason post hardware filtering, unwanted higher frequency components will be present along with frequency components in the channel signal associated with the breathing signal (which lies in the range 0.2-0.8 Hz), and the frequency components associated with the heart beat signal (0.9-2 Hz). However, another practical limitation is that design of a higher order filter or cascaded filters in hardware causes a delay in the output, resulting in slowing down of the system response. Thus, the required residual and precise filtering is performed by the system 102 using the software pre-processing block, as depicted in conjunction with FIG. 8. Also, however if entire filtering and preprocessing is based on software processing approach, this would unnecessary carry an amplified noise to the next level.

b) Amplifying the filtered plurality of segments of each of the first channel signal and the second channel using a preamplifier stage comprising a two-stage amplifier. The two-stage approach, as understood avoids saturation at first stage. The first stage is a preamplifier associated with the multi-feedback filter and the second stage is an instrumentation amplifier (IA) as depicted in hardware processing block 212 of FIG. 6. The gain of the first stage for example is 10, while the second stage can be configured to one of the gain values from 6, 11, and 21.

FIG. 7A through 7B, is an example design of the hardware processing block 212 of the system 102 comprising the MF-BPF providing filtering and I stage amplifier with gain G1 (FIG. 7A) cascaded with a second stage amplifier (an instrumentation amplifier in FIG. 7B)) with gain G2 followed by a level shifter (FIG. 7C). It can be understood by person skilled in the art that the same circuit design is repeated for Ch2 signal processing in the hardware processing block 212 and not repeated for brevity. The instrumentation amplifier is used as its Common Mode Rejection Ratio (CMRR) is very high (>100 dB), and high input impedance thus it is very suitable for biosignals, for which difference amplifier needs to be implemented. Moreover, simply by changing one resistance value ($R_G$—gain resistance), the amplifier gain can be modified. This arrangement of the hardware processing block 212 provides different selectable gains just by switching between different values of $R_G$. As can be seen from FIG. 7B, values of $R_G$ can be chosen to be one among R1, R2 and R3 using the jumpers JP1. Thus, system 102 utilizes a unique combination of hardware architecture of the MF-BPF followed by the instrumentation amplifier and then processing the channels signals through software preprocessing block, since only usage of software preprocessing is unable to extract the required information from the radar signals as raw radar signals are very noisy, are mostly saturated and have presence of DC to further degrade the signal.

Figure 8:
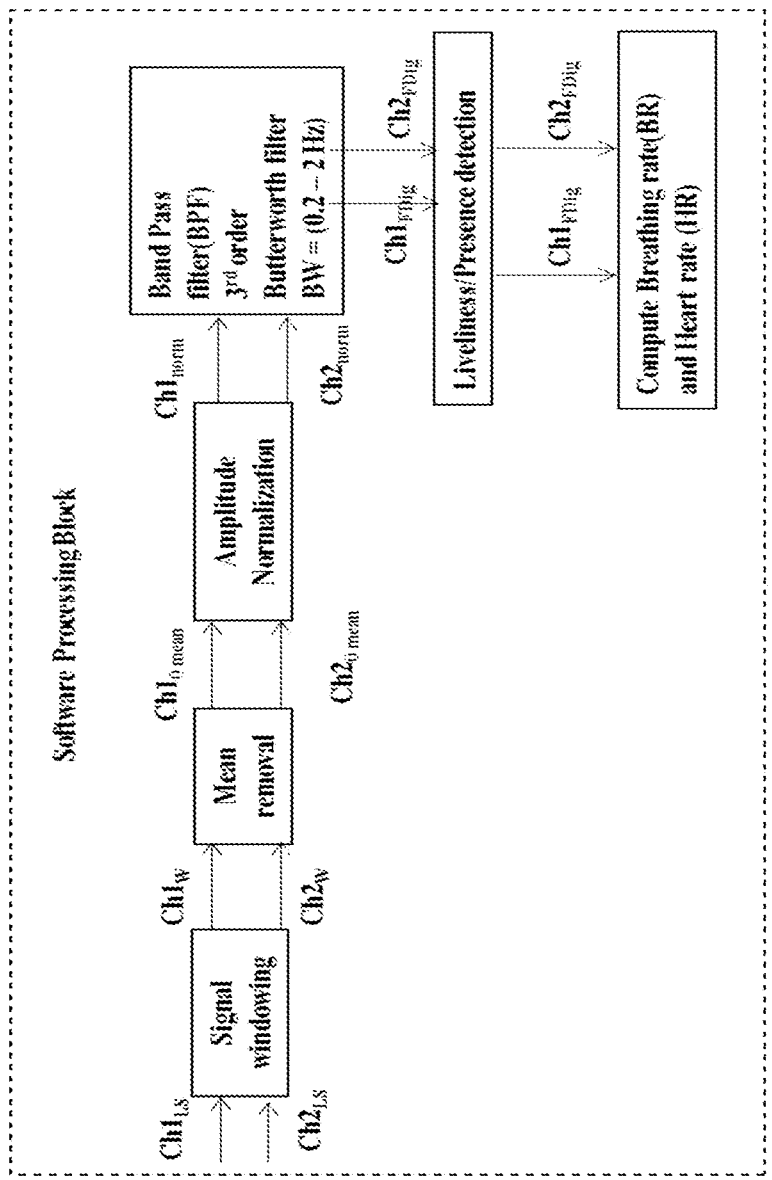
FIG. 8 depicts a software processing block of the system of FIG. 2 for preprocessing of signals captured by two spate radars of the DFR, in accordance with some embodiments of the present disclosure.

Once the channel signals are preprocessed by the hardware preprocessing block 212, at step 308 of the method 300, the one or more hardware processors 204 are configured to receive from the hardware preprocessing block 212, the first preprocessed plurality of segments of the first channel signal and the second channel signal. At step 310 of the method 300, the one or more hardware processors 204 are configured to sequentially perform a second preprocessing on the first preprocessed plurality of segments of the first channel signal and the second channel signal for a signal conditioning and a residual noise elimination processing using a software processing block. As depicted in FIG. 8 the software processing block receives signal from output of the circuit depicted in FIG. 7C (the level shifter) for both the channels. The software processing block comprises software processing block, which performs the signal conditioning and the residual noise elimination by applying a signal windowing, a mean removal and a software filtering. The incoming streams from the two channels are broken down (or segmented) into smaller sequences, each of which has a duration of 10 s, by making use of a windowing function. The is suitable as a complete breathing cycle can last up to 5 seconds, and as such a minimum of two cycles is required to correctly detect the underlying frequencies present in the sequence. The software filtering is performed using a third order Butterworth band pass filter on the first preprocessed plurality of segments of the first channel signal and the second channel signal. The third order Butterworth band pass filter providing software filtering, wherein the Butterworth filter is tuned to a second set of cut-off frequencies This is required to ensure, strict cut offs. Additionally, provides finer band limited signal in the range of 0.2 to 2 Hz, instead of 0 to 3 Hz, which cannot be guaranteed by the hardware filter of the hardware preprocessing block 212. Thereafter, the sequences are mean removed and amplitude normalized to complete the preprocessing block. The software processing block also includes presence detection and HR/BR computation block, explained in succeeding steps.

Upon applying the software preprocessing, at step 312 of the method 300, the one or more hardware processors 204 are configured to analyze each of the second preprocessed plurality of segments associated with the first channel signal and the second channel signal to detect a plurality of presence segments indicative of a presence of subject or one or more absence segments indicative of absence of the subject in the observation space based on a presence detection technique. The presence is determined for the segments for which energy levels of each of the second preprocessed plurality of segments associated with the first channel signal and the second channel signal are above a predefined energy threshold. The presence is detected by calculating the energy present in the signal over a small duration of time (for example, 1 second), when the radar is placed 1.5 meter away from the human (subject's body). If the average signal energy per unit sample crosses a predefined threshold (0.1) for either channel, it implies that a human presence is detected at that distance. If, however the said energy per sample crosses 0.3, it means that the environment has disturbances and is noisy. The energy is computed using equation (1) below:

$$\frac{1}{N}\sum_{n=0}^{N}|x(n)|^2, \qquad (1)$$

where x (n) is the acquired radar signal.

Once presence is detected in the observation space 112, at step 314 of the method 300, the one or more hardware processors 204 are configured to detect a quality of each of the plurality of presence segments by computing an Area Under Correlation (AUC) of each of the plurality of presence segments. Modules for signal processing in the memory 102, used by the system 102, considers real life conditions, where the signals are prone to lots of noises. Thus, quality of the signals being processed to extract HR and BR is strictly monitored by implementing signal quality check, effectively providing high accuracy in HR and BR measurements. Based on the computed AUC one or more segments among the plurality presence segments having the AUC below a first AUC threshold are discarded. A typical value of the first AUC threshold is 1 and is determined based on experimental data and is set to 1. The respiration and heart rates, both being periodic in nature, generate an auto correlation curve, the upper contour of which is triangular in nature. If the area under this curve (AUC) can be calculated, this would be an indicator of how good (in essence how periodic) the recorded data is. Two thresholds are selected for this purpose. If AUC>1.6, the recorded data quality is very good, and the HR and BR computation can proceed smoothly. If 1<AUC<1.6, then the quality of data is such that only the BR can be detected. If AUC<1, then the data quality is bad, and the corresponding data is discarded.

The method disclosed herein provides the signal quality check, as the same is prerequisites for HR and BR computation in real life scenarios due to presence of various motion artifacts other than the required signal. Also, signal quality check is required for null/optimum point which cannot be determined precisely for non-rigid object like human. It can be understood by person skilled in the art that phase of a baseband signal of a CW radar (DFR 214 herein) is the sinusoidal function of the summation of the distance from the target (i.e., human or subject herein) and its chest wall movement. The amplitude of chest wall movement, corresponding to the displacement due to respiration is small as compared to the carrier wavelength of a radar. Thus, small angle approximation technique for phase demodulation can be used. When the phase shift due to distance from the target is an odd multiple of pi/2

$$\left(\text{or } \frac{\pi}{2}\right),$$

optimum detection occurs. The baseband output becomes a linear function of time varying chest wall movement. Conversely, for phase shift being an even multiple of pi/2, null detection occurs. These null and optimum points alternate by a distance of one-eighth times the transmitting wavelength (lambda). Since the human body is a non-rigid object, so even if the distance between the radar and human body is fixed, then also there exists variations in the same and thus the optimal/null positioning of the subject (in front of the radar) is not feasible. Additionally, as system 102 utilizes independent radars with independent channels (not I-Q) radars, thus determining optimum channel is out of question. Due to these reasons, system 102 implements signal quality check, which determines which channel has a better signal quality compared to the other at the current time window.

For all the plurality of presence segments satisfying the quality criteria, at step 316 of the method 300, the one or more hardware processors 204 are configured to determine whether the AUC of each of the plurality of presence segments, having the AUC above or equal to the first AUC threshold, are i) above or ii) equal or below a second AUC threshold, wherein:

a) At step 318, a first set of presence segments among the plurality of presence segments having the AUC above the second AUC threshold are utilized for simultaneously determining a Hear Rate (HR) and a Breath Rate (BR) of the subject to detect and monitor the liveliness of the subject, as explained in conjunction with process depicted FIG. 4 b) At step 320, a second set of presence segments among the plurality of presence segments having the AUC below or equal to the second AUC threshold are utilized for determining only the BR rate to detect and monitor the liveliness of the subject, as explained in conjunction with process depicted FIG. 5

At step 322 of the method 300, the one or more hardware processors 204 are configured to generate an alert for at least one of: i) the determined HR is below a Liveliness HR threshold, and ii) the determined BR is below a liveliness BR threshold. The alert generated can be a beep sound by the system 102 in the observation space as well as to a remote observer monitoring the HR and BR of the subject. Further, the alert can be a notification sent on personal devices such as mobiles of a remote observer, one or more attendants associated with the subject and if required, to personal devices of the subject himself/herself. Typically:

a) HR<60 beats per minute is bradycardia, that is to be alerted, or HR>100 beats per minute is tachycardia, that is also to be alerted.
b) If the HR<30 and BR<5 breaths for more than 60 seconds, then high level of alert to be notified.

Referring now to FIG. 4 to the steps of process 400 indicate determination of the HR of the subject from the first set of presence segments having the AUC above the second AUC threshold. The steps comprise:

a) Filtering (402) each of the first set of presence segments of the first channel signal and the second channel using a third order Butterworth band pass filter tuned to a third set of cut-off frequencies tuned to select the frequency components of each of the plurality of presence segments that are associated with HR. The third set of cut of frequencies values are required to extract the heartbeat signal, which lies in the range (0.9-2 Hz).
b) Computing (404) frequency spectrums (FSs) of each of the filtered first set of presence segments of the first channel signal and the second channel signal by windowing each of the filtered first set of presence segments in accordance with a predefined window length with the windowed plurality of segments of the first channel signal and the second channel signal having a predefined overlap percentage. The typical window length is WinLen=2.5 Sec, 30% Overlap. Since 1 heart-beat approximately takes 1 sec to complete, the window length is selected so as to ensure the presence of at least 2 heart beat cycles, and so 2.5 sec is optimal for window length. The 30% overlap ensures decreasing the noises while performing frequency spectrum analysis on consecutive windows.

c) Summing (406) the FSs of each of the windowed first set of segments of the first channel signal and the second channel signal, as provided in example equation 2 using Fast Fourier Transform (FFT).

$$F_{Add} = \Sigma_{Win=1}^{N} FFT(Ch_{1,win}) + \Sigma_{Win=2}^{N} FFT(Ch_{2,win}) \quad (2)$$

d) Identifying (408) a first frequency in Hertz, at which maximum amplitude is observed in the summed FSs.
e) Determining (410) the HR of the subject by converting the determined frequency in Hertz to beats per minute by multiplying it by 60, as in equation 3 below:

$$HR = \max(FFT_{Add}) \times 60 \quad (3)$$

Thus, the HR extraction process starts by passing the generated sequences from the preprocessing block into third order Butterworth band pass filters to filter out frequencies beyond the required range (1 Hz-2 Hz). The filtered sequences are fed into a signal detrending block. This block fits tenth order polynomials on the filtered sequences and subtracts them from the same. This effectively removes the slowly varying signal components embedded in the sequences. The detrended sequence is subjected to a quality check. Following the quality check, the sequences from both radars are chopped up to segments of 2.5 seconds each, with a 30% overlap between adjacent segments. Frequency spectrum representations of each of those segments are taken and added up to form a composite frequency domain representation of the entire sequence. Detecting the peak in the said composite representation helps detect the HR present in the sequence. The sequence is finally checked for the presence of BR harmonics, which after being removed, finally generates the required HR.

Further, determining the BR of the subject from one of i) the first set of presence segments having AUC above the second AUC threshold and ii) the second set of presence segments having AUC below or equal to the second AUC threshold as depicted in FIG. 5 comprises:

a) Filtering (502) each of the first set of presence segments and the second set of presence segments of the first channel signal and the second channel signal using a third order Butterworth band pass filter tuned to a fourth set of cut-off frequencies to select the frequency components of each of the plurality of presence segments that are associated with BR. The fourth set of cut of frequencies values are required to extract the breathing signal, which lies in the range (0.2-0.8 Hz).
b) Selecting (504) optimal channel among the first channel signal and the second channel signal based on the AUC, wherein the selected optimal channel has a greater AUC. It has been found that data from each channel of the dual radar setup is not equally desirable for extraction of the BR. Fortunately, the signal generated from a radar due to the bodily movement associated with breathing has certain characteristics as identified earlier works that help to identify the better channel for BR extraction if multiple options are available. The channel that is detected to be optimal is exclusively used for BR extraction. The optimal channel sequence is first band pass filtered by a third order Butterworth filter to include frequencies in the range 0.2 Hz-0.8 Hz. The frequency spectrum of the resulting sequence has a distinctly identifiable peak, the detection of which directly generates the BR frequency, and subsequently the actual BR.

c) Computing (506) FSs of the optimal channel of each of the windowed plurality of segments of the first channel signal and the second channel signal.

d) Identifying (508) a second frequency in Hertz, at which maximum amplitude is observed in the FSs.

e) Determining (510) the BR by converting the identified frequency in Hertz to breaths per minute by multiplying it by 60.

In an embodiment, the first preprocessed plurality of segments of the first channel signal and the second channel signal are encoded/encrypted and transmitted to an external data analytics system over the MQTT communication interface. The encoded first preprocessed plurality of segments of the first channel signal and the second channel signal are decoded at the external data analytics system end, providing secure data transfer and maintain data privacy. The system can be configured to choose onboard or off board processing; thus processing being done on the system and/or remotely as well. So, in addition to the system being a liveliness monitor, it can also serve as a portable node for remote monitoring and maintaining continuous health records for subjects. The system can be implemented on a sensor node among a plurality of sensor nodes in the IOT network, thus providing a standalone sensor node with full processing capability along with securely data off boarding capability.

Experimental Results:

Table 1 below depicts subject wise mean absolute error (MAE)+/−standard deviation (SD) (in parenthesis) for HR and BR detected for 14 subjects using the system disclosed herein.

TABLE I

| Subject | BR MAE | HR MAE |
| --- | --- | --- |
| S1 | 1 ± (0.71) | 3.13 ± (2.86) |
| S2 | 1 ± (0.71) | 8.13 ± (4.72) |
| S3 | 1 ± (1.41) | 4.38 ± (4.33) |
| S4 | 2 ± (0.71) | 7.5 ± (4.96) |
| S5 | 1 ± (1.41) | 3.13 ± (2.17) |
| S6 | 1 ± (0.71) | 3.13 ± (3.9) |
| S7 | 2 ± (2.12) | 1.25 ± (1.08) |
| S8 | 1 ± (0.71) | 1.25 ± (1.08) |
| S9 | 2 ± (1.41) | 2.5 ± (2.86) |
| S10 | 2 ± (1.41) | 5.63 ± (5.63) |
| S11 | 1 ± (0.71) | 1.25 ± (1.08) |
| S12 | 1 ± (1.41) | 8.13 ± (9.62) |
| S13 | 1 ± (0.71) | 3.75 ± (1.88) |
| S14 | 1 ± (0.71) | 0.63 ± (1.08) |

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method for unobtrusive liveliness detection and monitoring using Dual Frequency Radar (DFR) in an Internet of Things (IOT) network, the method comprising:

receiving, by one or more hardware processors of a sensor node among a plurality of sensor nodes in the IOT network, a first channel signal captured by a first radar of the DFR and a second channel signal captured by a second radar of the DFR, wherein the first radar operates at a first frequency designed to capture chest movement of a subject due to heartbeat activity and the second radar operates at a second frequency designed to capture chest movement of the subject due to breathing activity, and wherein the DFR is positioned to cover an observation space for liveliness monitoring of the subject present in the observation space;

segmenting in time domain, by the one or more hardware processors, each of the first channel signal and the second channel signal into a plurality of segments in accordance with a predefined segment interval, wherein the predefined segment interval is selected to cover time corresponding to at least two breathing cycles;

transmitting, by the one or more hardware processors, the plurality of segments of the first channel signal and the second channel signal to a hardware preprocessing block to perform a first preprocessing on the plurality of segments of the first channel signal and the second channel signal to provide signal conditioning;

receiving, by the one or more hardware processors, from the hardware preprocessing block the first preprocessed plurality of segments of the first channel signal and the second channel signal;

sequentially performing a second preprocessing, by the one or more hardware processors, on the first preprocessed plurality of segments of the first channel signal and the second channel signal for signal conditioning and residual noise elimination using a software processing block;

analyzing, by the one or more hardware processors, each of the second preprocessed plurality of segments associated with the first channel signal and the second channel signal to detect a plurality of presence segments indicative of a presence of subject or one or more absence segments indicative of absence of the subject in the observation space based on a presence detection technique, wherein the detected one or more absence segments are discarded;

detecting, by the one or more hardware processors, a quality of each of the plurality of presence segments by computing an Area Under Correlation (AUC) of each of the plurality of presence segments, wherein one or more segments among the plurality presence segments having the AUC below a first AUC threshold are discarded;

determining, by the one or more hardware processors, whether the AUC of each of the plurality of presence segments, having the AUC above or equal to the first AUC threshold, are i) above or ii) equal or below a second AUC threshold, wherein a first set of presence segments among the plurality of presence segments having the AUC above the second AUC threshold is utilized for simultaneously determining a Hear Rate (HR) and a Breath Rate (BR) of the subject to detect and monitor the liveliness of the subject (318); and a second set of presence segments among the plurality of presence segments having the AUC below or equal to the second AUC threshold is utilized for determining the BR rate to detect and monitor the liveliness of the subject (320); and generating, by the one or more hardware processors, an alert for at least one of: i) if the determined HR is below a Liveliness HR threshold, and ii) if the determined BR is below a liveliness BR threshold.

2. The method of claim 1, wherein the first preprocessing comprises:

filtering the plurality of segments of each of the first channel signal and the second channel using a hardware multi-feedback band pass filter, wherein a first set of cut-off frequencies of the hardware band pass filter are tuned to capture frequency components corresponding to the chest movement due to the breathing activity and the heartbeat activity of the subject and eliminate inherent Direct Current (DC) component present in the first channel signal and the second channel signal of the DFR; and amplifying the filtered plurality of segments of each of the first channel signal and the second channel using a preamplifier stage comprising a two-stage amplifier.

3. The method of claim 1, wherein the software processing block performs the signal conditioning and the residual noise elimination by applying a signal windowing technique, a mean removal and a software filtering using a third order Butterworth band pass filter on the first preprocessed plurality of segments of the first channel signal and the second channel signal, and wherein the third order Butterworth band pass filter is tuned to a second set of cut-off frequencies.

4. The method of claim 1, wherein the presence detection technique detects the presence or the absence of the subject in the observation space by:

determining energy levels of each of the second preprocessed plurality of segments associated with the first channel signal and the second channel signal; and indicating the presence of the subject if the determined energy levels are above a predefined energy threshold.

5. The method of claim 1, wherein determining the HR of the subject from the first set of presence segments having the AUC above the second AUC threshold comprises:

a) filtering each of the first set of presence segments of the first channel signal and the second channel using a third order Butterworth band pass filter tuned to a third set of cut-off frequencies tuned to select the frequency components of each of the plurality of presence segments that are associated with the HR;

b) computing frequency spectrums (FSs) of each of the filtered first set of presence segments of the first channel signal and the second channel signal by windowing each of the filtered first set of presence segments in accordance with a predefined window length with the windowed plurality of segments of the first channel signal and the second channel signal having a predefined overlap percentage;

c) summing the FSs of each of the windowed first set of segments of the first channel signal and the second channel signal;

d) identifying a first frequency in Hertz, at which maximum amplitude is observed in the summed FSs; and e) determining the HR of the subject by converting the determined frequency in Hertz to beats per minute by multiplying it by 60.

6. The method of claim 1, wherein determining the BR of the subject from one of i) the first set of presence segments having AUC above the second AUC threshold and ii) the second set of presence segments having AUC below or equal to the second AUC threshold comprises:
   a) filtering each of the first set of presence segments and the second set of presence segments of the first channel signal and the second channel signal using a third order Butterworth band pass filter tuned to a fourth set of cut-off frequencies to select the frequency components of each of the plurality of presence segments that are associated with BR;
   b) selecting an optimal channel among the first channel signal and the second channel signal based on the AUC, wherein the selected optimal channel has a greater AUC;
   c) computing FSs of the optimal channel of each of the windowed plurality of segments of the first channel signal and the second channel signal;
   d) identifying a second frequency in Hertz, at which maximum amplitude is observed in the FSs; and
   e) determining the BR by converting the identified frequency in Hertz to breaths per minute by multiplying it by 60.

7. The method of claim 1, further comprising encoding the first preprocessed plurality of segments of the first channel signal and the second channel signal and transmitting the encoded first preprocessed plurality of segments of the first channel signal and the second channel signal to an external data analytics system over an Message Queuing Telemetry Transport (MQTT) communication interface, wherein the encoded first preprocessed plurality of segments of the first channel signal and the second channel signal are decoded at the external data analytics system end.

8. A system for unobtrusive liveliness detection and monitoring using Dual Frequency Radar (DFR) in an Internet of Things (IOT) network, the system comprising:
   a memory storing instructions;
   one or more Input/Output (I/O) interfaces; and
   one or more hardware processors coupled to the memory via the one or more I/O interfaces, wherein the one or more hardware processors are configured by the instructions to:
      receive a first channel signal captured by a first radar of the DFR and a second channel signal captured by a second radar of the DFR, wherein the first radar operates at a first frequency designed to capture chest movement of a subject due to heartbeat activity and the second radar operates at a second frequency designed to capture chest movement of the subject due to breathing activity, and wherein the DFR is positioned to cover an observation space for liveliness monitoring of the subject present in the observation space;
      segment in time domain each of the first channel signal and the second channel signal into a plurality of segments in accordance with a predefined segment interval, wherein the predefined segment interval is selected to cover time corresponding to at least two breathing cycles;
      transmit the plurality of segments of the first channel signal and the second channel signal to a hardware preprocessing block of the system 102 to perform a first preprocessing on the plurality of segments of the first channel signal and the second channel signal to provide signal conditioning;
      receive from the hardware preprocessing block the first preprocessed plurality of segments of the first channel signal and the second channel signal;
      sequentially perform on the first preprocessed plurality of segments of the first channel signal and the second channel signal for signal conditioning and residual noise elimination using a software processing block;
      analyze each of the second preprocessed plurality of segments associated with the first channel signal and the second channel signal to detect a plurality of presence segments indicative of a presence of subject or one or more absence segments indicative of absence of the subject in the observation space based on a presence detection technique, wherein the detected one or more absence segments are discarded;
      detect a quality of each of the plurality of presence segments by computing an Area Under Correlation (AUC) of each of the plurality of presence segments, wherein one or more segments among the plurality presence segments having the AUC below a first AUC threshold are discarded;
      determine whether the AUC of each of the plurality of presence segments, having the AUC above or equal to the first AUC threshold, are i) above or ii) equal or below a second AUC threshold, wherein
         a first set of presence segments among the plurality of presence segments having the AUC above the second AUC threshold is utilized for simultaneously determining a Hear Rate (HR) and a Breath Rate (BR) of the subject to detect and monitor the liveliness of the subject; and
         a second set of presence segments among the plurality of presence segments having the AUC below or equal to the second AUC threshold is utilized for determining the BR rate to detect and monitor the liveliness of the subject; and
      generate an alert for at least one of: i) if the determined HR is below a Liveliness HR threshold, and ii) if the determined BR is below a liveliness BR threshold.

9. The system of claim 8, wherein the first preprocessing by the hardware processing block comprises:
   filtering the plurality of segments of each of the first channel signal and the second channel using a hardware multi-feedback band pass filter, wherein a first set of cut-off frequencies of the hardware band pass filter are tuned to capture frequency components corresponding to the chest movement due to the breathing activity and the heartbeat activity of the subject and eliminate inherent Direct Current (DC) component present in the first channel signal and the second channel signal of the DFR; and
   amplifying the filtered plurality of segments of each of the first channel signal and the second channel using a preamplifier stage comprising a two-stage amplifier.

10. The system of claim 8, wherein the one or more hardware processors are configured to perform the signal conditioning and the residual noise elimination by applying a signal windowing technique, a mean removal and a software filtering using a third order Butterworth band pass filter on the first preprocessed plurality of segments of the first channel signal and the second channel signal, and wherein the third order Butterworth band pass filter is tuned to a second set of cut-off frequencies.

11. The system of claim 8, wherein the one or more hardware processors are configured to detect the presence or the absence of the subject in the observation space using the presence detection technique by:
  determining energy levels of each of the second preprocessed plurality of segments associated with the first channel signal and the second channel signal; and
  indicating the presence of the subject if the determined energy levels are above a predefined energy threshold.

12. The system of claim 8, wherein the one or more hardware processors (204) are configured to determine the HR of the subject from the first set of presence segments having the AUC above the second AUC threshold by:
  a) filtering each of the first set of presence segments of the first channel signal and the second channel using a third order Butterworth band pass filter tuned to a third set of cut-off frequencies tuned to select the frequency components of each of the plurality of presence segments that are associated with the HR;
  b) computing frequency spectrums (FSs) of each of the filtered first set of presence segments of the first channel signal and the second channel signal by windowing each of the filtered first set of presence segments in accordance with a predefined window length with the windowed plurality of segments of the first channel signal and the second channel signal having a predefined overlap percentage;
  c) summing the FSs of each of the windowed first set of segments of the first channel signal and the second channel signal;
  d) identifying a first frequency in Hertz, at which maximum amplitude is observed in the summed FSs; and
  e) determining the HR of the subject by converting the determined frequency in Hertz to beats per minute by multiplying it by 60.

13. The system of claim 8, wherein the one or more hardware processors are configured to determine the BR of the subject from one of i) the first set of presence segments having AUC above the second AUC threshold and ii) the second set of presence segments having AUC below or equal to the second AUC threshold by:
  a) filtering each of the first set of presence segments and the second set of presence segments of the first channel signal and the second channel signal using a third order Butterworth band pass filter tuned to a fourth set of cut-off frequencies to select the frequency components of each of the plurality of presence segments that are associated with BR;
  b) selecting an optimal channel among the first channel signal and the second channel signal based on the AUC, wherein the selected optimal channel has a greater AUC;
  c) computing FSs of the optimal channel of each of the windowed plurality of segments of the first channel signal and the second channel signal;
  d) identifying a second frequency in Hertz, at which maximum amplitude is observed in the FSs; and
  e) determining the BR by converting the identified frequency in Hertz to breaths per minute by multiplying it by 60.

14. The system of claim 8, wherein the one or more hardware processors are further configured to encode the first preprocessed plurality of segments of the first channel signal and the second channel signal and transmit the encoded first preprocessed plurality of segments of the first channel signal and the second channel signal to an external data analytics system over an Message Queuing Telemetry Transport (MQTT) communication interface, wherein the encoded first preprocessed plurality of segments of the first channel signal and the second channel signal are decoded at the external data analytics system end.

15. One or more non-transitory machine readable information storage mediums comprising one or more instructions, which when executed by one or more hardware processors causes a method for:
  receiving by a sensor node among a plurality of sensor nodes in the IOT network, a first channel signal captured by a first radar of the DFR and a second channel signal captured by a second radar of the DFR, wherein the first radar operates at a first frequency designed to capture chest movement of a subject due to heartbeat activity and the second radar operates at a second frequency designed to capture chest movement of the subject due to breathing activity, and wherein the DFR is positioned to cover an observation space for liveliness monitoring of the subject present in the observation space;
  segmenting in time domain each of the first channel signal and the second channel signal into a plurality of segments in accordance with a predefined segment interval, wherein the predefined segment interval is selected to cover time corresponding to at least two breathing cycles;
  transmitting the plurality of segments of the first channel signal and the second channel signal to a hardware preprocessing block to perform a first preprocessing on the plurality of segments of the first channel signal and the second channel signal to provide signal conditioning;
  receiving from the hardware preprocessing block the first preprocessed plurality of segments of the first channel signal and the second channel signal;
  sequentially performing a second on the first preprocessed plurality of segments of the first channel signal and the second channel signal for signal conditioning and residual noise elimination using a software processing block;
  analyzing each of the second preprocessed plurality of segments associated with the first channel signal and the second channel signal to detect a plurality of presence segments indicative of a presence of subject or one or more absence segments indicative of absence of the subject in the observation space based on a presence detection technique, wherein the detected one or more absence segments are discarded;
  detecting a quality of each of the plurality of presence segments by computing an Area Under Correlation (AUC) of each of the plurality of presence segments, wherein one or more segments among the plurality presence segments having the AUC below a first AUC threshold are discarded;
  determining whether the AUC of each of the plurality of presence segments, having the AUC above or equal to the first AUC threshold, are i) above or ii) equal or below a second AUC threshold, wherein
    a first set of presence segments among the plurality of presence segments having the AUC above the second AUC threshold is utilized for simultaneously determining a Hear Rate (HR) and a Breath Rate (BR) of the subject to detect and monitor the liveliness of the subject (318); and
    a second set of presence segments among the plurality of presence segments having the AUC below or equal to the second AUC threshold is utilized for determining the BR rate to detect and monitor the liveliness of the subject (320); and generating an alert for at least one of: i) if the determined HR is below a Liveliness HR threshold, and ii) if the determined BR is below a liveliness BR threshold.

\* \* \* \* \*